United States Patent

Rains

Patent Number: 5,326,261
Date of Patent: Jul. 5, 1994

[54] DENTAL MARKING PRODUCT

[76] Inventor: Michael D. Rains, 9209 Colima Rd., Whittier, Calif. 90605

[21] Appl. No.: 5,766

[22] Filed: Jan. 15, 1993

[51] Int. Cl.$^5$ ............................ A61C 3/00; A61C 9/00
[52] U.S. Cl. ...................................... 433/141; 433/70; 433/3; 401/49
[58] Field of Search .................. 433/3, 68, 70, 75, 141; 401/49; 132/320

[56] References Cited

U.S. PATENT DOCUMENTS

| | | |
|---|---|---|
| D. 206,641 | 1/1967 | Hill . |
| 3,068,571 | 12/1962 | Thompson ........................... 433/141 |
| 3,588,260 | 6/1971 | Caywood et al. ..................... 401/49 |
| 3,686,762 | 8/1972 | Sutter . |
| 4,264,308 | 4/1981 | Tanaka ................................ 433/70 |
| 4,725,228 | 2/1988 | Andrews . |
| 4,805,646 | 2/1989 | Shimenkov . |
| 4,834,654 | 5/1989 | Nussbaum . |
| 5,044,383 | 9/1991 | Alessio et al. . |

FOREIGN PATENT DOCUMENTS 0327803  8/1989  European Pat. Off. .
1518137  7/1978  United Kingdom .

Primary Examiner—John J. Wilson
Assistant Examiner—Nicholas D. Lucchesi
Attorney, Agent, or Firm—Knobbe Martens Olson & Bear

[57] ABSTRACT

A disposable dental marking product comprising a elongated shaft having a first end representing a gripping area for a user's fingers and a second end directly covered with a composition of marking chemicals representing a writing area.

12 Claims, 1 Drawing Sheet

DENTAL MARKING PRODUCT

BACKGROUND OF THE INVENTION

The present invention relates to a marking product. More particularly it relates to a marking product used by dentists and orthodontists.

Dentists and orthodontists often require in their practice, a product capable of marking teeth, braces, other orthodontic apparatuses, dentures, partial dentures, bridges or restorations. For instance, when removing braces from a patient, it is often necessary for the orthodontist to leave reference marks on the wires to ensure accurate cutting or bending for adjustments. Further, it is also often necessary for dentists to place reference marks on dentures, partial dentures and various other dental appliances for adjustment procedures. Thus, it is common practice for dentists and orthodontists to use a marking product.

There are numerous types of marking apparatuses used by dentists and orthodontists presently. For instance, products such as "China Markers" or wax pencils are frequently utilized by dentists and orthodontists today. A China Marker is a type of pencil which comprises a colored wax circumferentially wrapped by a helically wound strand of paper. When the colored wax is depleted, the paper is unwrapped to expose a new surface of wax. Thus, one China Marker could last a fairly long time. However, this prior marker has the disadvantage in that it is not orally hygienic. For example, one marker is often used on numerous patients containing various infections. The current fear of many patients of contacting HIV, the virus that causes AIDS, makes a more hygienic product particularly desirable. Due to the cost of manufacturing such a prior marker, it would be economically disadvantageous to discard the marker after a single use.

Thus there appears to be a need for a dental marking product which is more orally hygienic than prior art markers.

SUMMARY OF THE INVENTION

The present invention, relates to a disposable dental marking product capable of marking teeth or orthodontic apparatuses. The present invention comprises an elongated shaft made out of wood or other suitable material having a composition of markable chemicals placed directly on one end. The present marking product is simple in construction and economical to manufacture. Preferably, the present invention is manufactured by conforming a small piece of wood into an elongated shaft. One end of the shaft is then dipped into a hot composition of marking chemicals and then allowed to cool. This simplistic and economical manufacturing process creates a product which is economical to dispose of after each use. Disposability is very important in the medical field because of the need to maintain a high level of sterility.

The novel features considered as characteristic for the invention are set forth in particular in the appended claims. The invention itself, however, both as to its construction and its method of operation together with additional objects and events thereof, will be best understood from the following description of the specific embodiment when read in connection with the accompanying drawings.

DESCRIPTION OF THE PREFERRED EMBODIMENT

Figure 1:
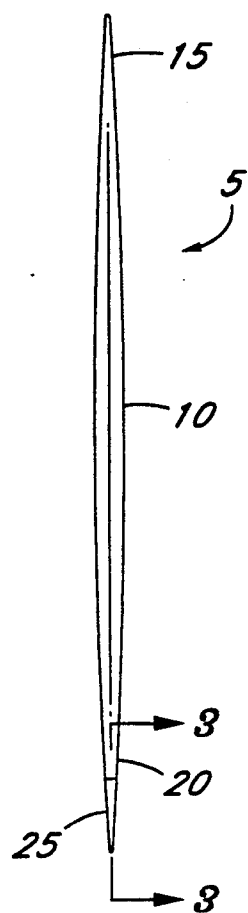
FIG. 1 is a perspective view of the dental marking product of the present invention.
Figure 2:
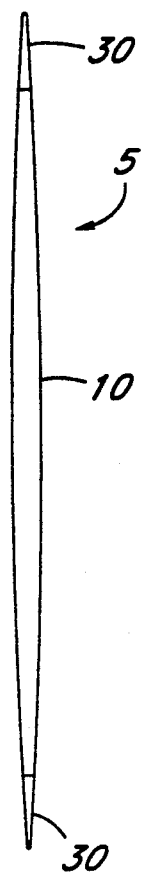
FIG. 2 is an alternate embodiment of the dental marking product of the present invention.
Figure 3:
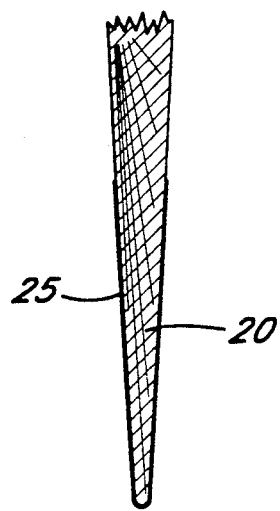
FIG. 3 is a cross-sectional view taken along lines 3—3 of FIG. 1.

FIGS. 1 and 3 disclose an dental marking product comprising a elongated shaft 5. The elongated shaft 5 has a midsection 10 having a square cross section (not shown) with rectangular sides. However, it is conceivable to have the midsection 10 represent a cylindrical member as shown in FIG. 2. The shaft 5 is made out of wood, but other materials such as a light-weight plastic is also suitable. In one application, the shaft 5 is approximately 2.5 inches long with a midsection 10 of approximately 0.125 of an inch thick. However, the length of the shaft 5 can range from 1.5–6 inches and the thickness of the midsection 10 can range from 0.125–0.2 of an inch.

Referring to FIG. 1, the midsection 10 tapers in thickness at a first end representing a frescos-conical gripping end 15. However, it is also conceivable to have the gripping end 15 the same thickness as the midsection 10. In one application, the gripping end 15 is approximately 0.5 of an inch long and tapers in thickness from 0.125 to 0.0625 of an inch at its outermost region. The length of the gripping end 15 can range from 0.34 to 1 inch. The thickness of the gripping end 15 can range from 0.0625–0.3 of an inch. However, it is preferable that the gripping end 15 be thick enough so that the user can securely grip the marker.

The midsection 10 also tapers in thickness at a second end representing a frusto-conical writing end 20. The dimension of the writing end 20 are preferably the same as the gripping end 15. However, the writing end 20 is preferably not as thick as the midsection 10 because a substantially pointed end ensures accurate markings.

A composition of marking chemicals 25 is placed directly on the writing end 20 of the shaft 5. The markable chemicals 25 can comprise generally non-toxic waxes and oils, such as crayons, lipstick or mineral oil. Any chemical which is safe for topical administration of a patient's oral cavity may be suitable. In one application, the composition of markable chemicals 25 comprises 1 lb. of cocoa butter, 1 lb. of bees' wax and ¼ lb. of FD&C Yellow #5. Any standard brand of cocoa butter, bees' wax and pigment color is suitable as long as it is safe for oral administration.

The ratio of the various materials may be varied as desired. For instance, if a darker marking chemical is desired, a greater amount of color pigment may be added. Likewise, if a more sticker substance is desired, a greater amount of bees' wax may preferably be used. Preferably, the cocoa butter comprises 30–60 percent of the total composition. The bees' wax preferably comprises 30–60 percent of the total composition. The color pigment preferably comprises 10–15 percent of the total composition.

In the preferred embodiment, there should be enough markable chemicals 25 on the writing end 20 of the elongated shaft 5 to leave a substantially identifiable mark on the tooth or the orthodontic apparatus.

The present invention is preferably manufactured by dipping the writing end 20 of the shaft 5 in the marking chemicals 25 while the chemicals are in a liquid form. The shaft 5 is then removed from the chemicals and allowed to cool. Once the chemicals have cooled, the composition should preferably be in a colored semi-solid form. The consistency of the composition should preferably be capable of securing the chemicals on the writing end 20 of the shaft 5. But when the chemicals are rubbed against a surface, the chemicals should disengage from the writing end 20 and transferred to the desired area, leaving a reference mark.

FIG. 2 shows another embodiment of the present invention where the elongated shaft 5 comprises a cylindrical midsection 10 and two tapering conical ends. Both ends of the embodiment are directly covered with marking chemicals 30 similar to a "Q-tip" arrangement. The dimension of this embodiment is substantially the same as the prior embodiment and as such will not be repeated. This configuration maximizes the marking capabilities of the invention. When all the chemicals 30 on one end are used up, the dentist or orthodontist can simply rotate the shaft 5 about an axis perpendicular to the longitudinal axis of the shaft 5, to expose an end containing a fresh supply of marking chemicals 30.

In operation, when an orthodontist desires to mark the braces of a patient, he will hold the elongated shaft 5 at its gripping end 15, preferably spaced from its outermost end to ensure stability in the use of the product. The user can grip anywhere along the gripping end 15 as long as he can maintain control over the shaft 5. A user must be able to securely handle the shaft 5 for precise marking applications. The writing end 20 of the shaft 5 can then be inserted into the patient's mouth so that the marking chemicals 25 placed at this end can be applied to the desired area. Application of the marking chemicals 25 encompasses the rubbing of the chemicals 25 adjacent the tooth or apparatus so that the chemicals 25 can be transferred from the shaft 5 to the desired area. Once the required marking for a patient is completed, the dental marking product can be disposed of for hygienic reasons.

If numerous marks are required, several marking products may be used on a single patient, or the second embodiment of the present invention may be utilized. The second embodiment allows dentists and orthodontists to utilize both ends of the product to carry out the marking operation as discussed previously. However, even if both ends of the second embodiment are not used, it is highly desirable to limit the use of the product to a single patient.

What is claimed:

1. A disposable dental marking product consisting essentially of:
    a elongated shaft having a first end and a second end, said first end of said shaft being of sufficient dimensions to be gripped by a human hand; and
    a marking composition placed directly on said second end, said marking composition being a colored, semi-solid oil soluble material capable of being transferred directly to a tooth, an orthodontic apparatus or dentures by application thereto without the aid of any liquid.

2. The product of claim 1, wherein the length of said shaft is in the range of 1.5-6 inches and the thickness of said shaft is in the range of 0.125-0.2 of an inch.

3. A disposable dental marking product consisting essentially of:
    a elongated shaft having a first end and a second end, said first end of said shaft being of sufficient dimensions to be gripped by a human hand; and
    a marking composition placed directly on said second end, said marking composition being a colored, semi-solid material capable of being transferred to a tooth, an orthodontic apparatus or dentures by application thereto, wherein said marking composition comprises non-toxic oils and waxes.

4. The product of claim 3, wherein said composition comprises cocoa butter, bees' wax and color pigment.

5. The product of claim 4, wherein said cacao butter comprises 30-60 percent, said bees' wax comprises 30-60 percent and said color pigment comprises 10-15 percent of said marking composition.

6. A disposable dental marking product consisting essentially of:
    a elongated shaft having a first end and a second end, said shaft having a length in the range of 1.5-6 inches and a thickness in the range of 0.125-0.2 inches; and
    a marking composition placed directly on said second end, said marking composition being a colored, semi-solid oil soluble material capable of being transferred directly to a tooth, an orthodontic apparatus or dentures by application thereto without the aid of any liquid.

7. A disposable dental marking product consisting essentially of:
    an elongated shaft having a first end and a second end, said shaft having a length in the range of 1.5-6 inches and a thickens in the range of 0.125-0.2 inches; and
    a marking composition placed directly on said second end, said marking composition being a colored, semi-solid material capable of being transferred to a tooth, an orthodontic apparatus or dentures by application thereto, wherein said marking composition comprises 36-60 percent cocoa butter, 30-60 percent bees' wax and 10-15 percent color pigment.

8. A method of directly marking a tooth, an orthodontic apparatus or dentures in a mouth of a patient without the aid of any liquid using a disposable dental marking product having a first end that includes an area for gripping by fingers of a user thereof, a second end directly covered with a marking composition including a colored, semi-solid oil soluble material, said method comprising the following steps:
    gripping said marking product on said first end with said fingers;
    inserting said second end into said mouth of said patient;
    directly applying marks on said tooth or said orthodontic apparatus or said dentures by rubbing said marking composition on said tooth or said orthodontic apparatus or said dentures; and
    disposing said product after the applying step without reuse of said product.

9. The method of claim 8, wherein the gripping step comprises gripping said second end of said product close to but distanced from the outermost tip of said second end.

10. A method of directly marking a tooth, an orthodontic apparatus or dentures in a mouth of a patient without the aid of any liquid using a disposable dental marking product having a first end and a second end, each of said first and second ends being directly covered with a marking composition including a colored, semi-solid oil soluble material, said method comprising the following steps:

gripping said product about said first end with fingers of a user thereof;

inserting said second end into said mouth of said patient;

directly marking said tooth, said apparatus or said dentures with said marking composition; and disposing said marking product after the marking step without the reuse of said product.

11. The method of claim 10, wherein said marking step comprises rubbing said composition adjacent said tooth, said apparatus or said dentures.

12. A method for directly marking a tooth, an orthodontic apparatus or dentures in a mouth of a patient using a disposable dental marking product having a first end and a second end, each of said first and second ends being directly covered with a marking composition, said method comprising the following steps:

gripping said product about said first end with fingers of user thereof;

inserting said second end into said mouth of said patient;

directly marking said tooth, said apparatus or said dentures with said marking composition;

switching said first and second ends of said product such that said product is rotated about an axis perpendicular to a longitudinal access of said product;

gripping said product about said second end with said fingers;

inserting said first end into said mouth of said patient;

marking said tooth, said orthodontic apparatus or said dentures by rubbing said composition on said tooth, said orthodontic apparatus or said dentures; and disposing said marking product after the marking step without the reuse of said product.

* * * * *

UNITED STATES PATENT AND TRADEMARK OFFICE
CERTIFICATE OF CORRECTION

PATENT NO. : 5,326,261
DATED : July 5, 1994
INVENTOR(S) : Michael D. Rains

It is certified that error appears in the above-indentified patent and that said Letters Patent is hereby corrected as shown below:

```
Column 4, line 12, change "cacao" to --cocoa--.

Column 4, line 39, change "36-60" to --30-60--.
```

Signed and Sealed this

Twenty-seventh Day of December, 1994

Attest:

BRUCE LEHMAN

Attesting Officer     Commissioner of Patents and Trademarks